(12) United States Patent
Winter

(10) Patent No.: US 6,189,701 B1
(45) Date of Patent: Feb. 20, 2001

(54) METHOD AND DEVICE FOR PRODUCING PLASTIC HOLLOW BODIES

(75) Inventor: Horst Winter, Neutraubling (DE)

(73) Assignee: Krones AG (DE)

( * ) Notice: Under 35 U.S.C. 154(b), the term of this patent shall be extended for 0 days.

(21) Appl. No.: 09/446,937

(22) PCT Filed: Apr. 28, 1999

(86) PCT No.: PCT/EP99/02863

§ 371 Date: Dec. 28, 1999

§ 102(e) Date: Dec. 28, 1999

(87) PCT Pub. No.: WO99/58315

PCT Pub. Date: Nov. 18, 1999

(30) Foreign Application Priority Data

May 12, 1998  (DE) ............................................ 198 21 105

(51) Int. Cl.[7] ...................................................... B07C 5/00
(52) U.S. Cl. ..................... 209/523; 209/522; 209/529; 209/552; 209/559; 209/597; 198/406; 198/417
(58) Field of Search ................................. 209/522, 523, 209/524, 525, 526, 552, 597; 193/46; 198/406, 417

(56) References Cited

U.S. PATENT DOCUMENTS

| 4,693,375 |   | 9/1987 | Schweers . |   |
|---|---|---|---|---|
| 5,186,307 | * | 2/1993 | Doudement et al. | 198/454 |
| 5,248,045 | * | 9/1993 | Alvelda | 209/552 |

FOREIGN PATENT DOCUMENTS

| 19737527 | 4/1999 | (DE) . |
| 2-34322 | 7/1988 | (JP) . |

* cited by examiner

Primary Examiner—Donald P. Walsh
Assistant Examiner—Mark J. Beauchaine
(74) Attorney, Agent, or Firm—Tilton, Fallon, Lungmus & Chestnut

(57) ABSTRACT

Device and process for the manufacture of hollow plastic objects to screen out defective plastic preforms that are to be molded into their desired shape in a molding station before they reach the molding station, the conveyor track leading into the molding station comprising a screening area through which the preforms are conveyed in such a way that they are loosely supported on only one side, wherein screening apparatuses are provided in the screening area to screen out defective plastic preforms in response to signals from an inspection station.

27 Claims, 2 Drawing Sheets

METHOD AND DEVICE FOR PRODUCING PLASTIC HOLLOW BODIES

FIELD OF THE INVENTION

The invention relates to a device for the manufacture of hollow plastic objects, especially stretch-blown plastic bottles, with a conveyor track along which plastic preforms are transported in sequence past at least one inspection station to a molding station for molding the preforms into a desired shape.

BACKGROUND OF THE INVENTION

A type of device and a type of process for manufacturing hollow plastic objects are known in practice. It is customary, especially in the manufacture of plastic bottles, particularly PET bottles, to convey so-called preforms made of plastic from a repository to a molding station. This molding station may include, for example, a heating device in which preforms are heated to the temperature needed for the subsequent stretch blowing process. The final shape of the bottle is then created during the subsequent stretch blowing process.

However, a defectively manufactured preform can cause operating problems if it reaches the heating device and/or the stretch blowing device. For example, damage to the mouth area of a preform may result in leakage during the stretch blowing process. Consequently the preforms are moved past an inspection station in the shape of a mandrel wheel. The individual mandrels of this wheel penetrate the mouth of a preform and scan it mechanically so as to be able to detect certain defects in the mouth area. If a defect is detected, the machine is stopped and an operator must remove the defective preform. Consequently, an operator must be present and the machinery may be subject to downtimes that reduce its output. In addition, there is a risk that the penetrating action of the mandrel wheel may damage the plastic preforms.

SUMMARY OF THE INVENTION

Consequently, the objective of the invention is to further develop a generic device and a generic process so as to ensure that such drawbacks do not occur.

According to the invention, the device features a screening area in which the preforms are conveyed in such a way that they are loosely supported on only one side, and in which is provided a screening apparatus that moves plastic preforms that have been identified as being defective out of the row in response to signals from the inspection station.

The preforms are loosely supported on only one side as they move through the screening area. This enables the screening apparatus to move a plastic preform identified as being defective by the inspection station out of the row. This does not require that any substantial forces or tensions be overcome, as the preforms are only loosely supported in the screening area. An operator is no longer needed and the screening process can take place continuously. There is no need to interrupt production.

A lever-like guide that guides the plastic preforms in the screening area into a pivoted position is provided in an advantageous embodiment of the invention. Because of this pivoted position, it is possible to support the plastic preforms in the screening area on only side while continuing to guide them in a precise manner.

The plastic preforms can be pivoted to any degree, provided it is sufficient to ensure that they remain in their pivoted position. An angle of 50° against a vertical plane progressing in the direction of movement has proven to be especially advantageous.

The device according to the invention is especially suitable for use with plastic preforms that feature a collar in the mouth area. Such plastic preforms may, for example, be used in the manufacture of PET plastic bottles. This type of collar or neck ring is an area along the plastic preform with a larger diameter that allows the preform to be transported by suspending it from this collar. In an advantageous embodiment of the device according to the invention, the lever-like guide features a guide edge that engages the collars of the plastic preforms.

The pivoted position of the plastic preforms in the screening area may, for example, be generated by a surface against which the plastic preforms rest in a pivoted position. In an alternative form of the invention, a guide rail is provided that engages the lower portions of the plastic preforms so as to move them into the pivoted position.

The plastic preforms can be fed along the entire conveyor track in their unilaterally supported pivoted position. However, a method of conveyance that is particularly secure and space-saving comprises guide rails that support the plastic preforms at their collars from two sides. A break in one of these guide rails in the screening area through which the preforms are conveyed in a pivoted position allows for the removal of defective plastic preforms. The pivoted or tilted position in the screening area also provides for secure guidance when the guide rail is interrupted on the screening side.

If the plastic preforms are transported in areas outside the screening area in a primarily vertical position, i.e., a position located in a vertical plane, the lever-like guide is designed in such a way that the plastic preforms are placed into the pivoted position at the beginning of the screening area. In a design in which the lever-like guide consists of a surface, this surface is curved accordingly. If the lever-like guide is comprised, for example, of upper and lower guide rails, these rails are twisted in such a way that they transport the plastic preforms from their primarily vertical position to the pivoted position as they move along the conveyor track.

Guide rails according to the invention may have different shapes. However, it is especially advantageous if the guide rails feature support surfaces that conform to the shape of the collars and lateral surfaces of the plastic preforms. Such support surfaces are advantageously twisted in such a way that they follow the pivoting motion of the plastic preforms. This ensures especially secure guidance.

The screening apparatus can be executed in various ways. For example, a mechanism can be provided that interrupts the loose support of a plastic preform that has been identified as being defective in response to a signal from the inspection station, thus allowing the defective plastic preform to drop downward. However, a particularly simple screening apparatus can be achieved with a pusher that gives the plastic preform a lateral push in response to an error signal from at least one inspection station, thus disengaging the collar of the plastic preform from the guide rail. Disengaging the plastic preform from the guide rail causes the plastic preform that has been identified as being defective to slip downward and into a screening container, if provided. This type of design ensures that the adjacent plastic preforms are not affected by the screening process. The lateral push can be applied to the lateral surface of the plastic preform or to its mouth area.

The pusher may consist of a simple tappet. It may also be provided that the surface of the pusher that touches the preform during the screening process conforms to its external shape. In a simple design, the pusher comprises a prismatic surface that opens in a concave manner relative to the preform being screened out. This type of prismatic surface is easy to manufacture and causes the preform to become centered during the screening process.

The inspection station can be arranged directed in the screening area and can control the screening apparatus directly. A more detailed inspection can be performed if the inspection station is arranged upstream from the screening area and emits a time-delayed signal to the screening apparatus, with the time delay corresponding to the amount of a time a plastic preform needs to travel from the inspection station to the screening apparatus.

In a design of this nature, several inspection stations can be arranged in sequence to test various parameters of the plastic preforms, such as their lateral surfaces.

A fixed value may be established for the time delay between the inspection and the screening process. However, in an enhancement of the invention, an apparatus is provided that allows for monitoring the path between the inspection station and the screening station, thereby ensuring that the proper plastic preform can continue to be screened out at various transport speeds. This type of apparatus may comprise, for example, a multiple photoelectric barrier past which the plastic preforms are moved.

The plastic preforms can be moved along the conveyor track by means of driving mechanisms. This is easily achieved with a conveyor track that is inclined in the direction of transport, so that the plastic preforms are moved along the conveyor track as a result of their own weight.

To ensure a secure inspection by the inspection device, a driving mechanism can be provided in the inspection area which guarantees a defined speed.

BRIEF DESCRIPTION OF THE DRAWINGS

An execution of the device according to the invention is described below on the basis of the drawings.

DETAILED DESCRIPTION OF THE PREFERRED EMBODIMENT

Figure 1:
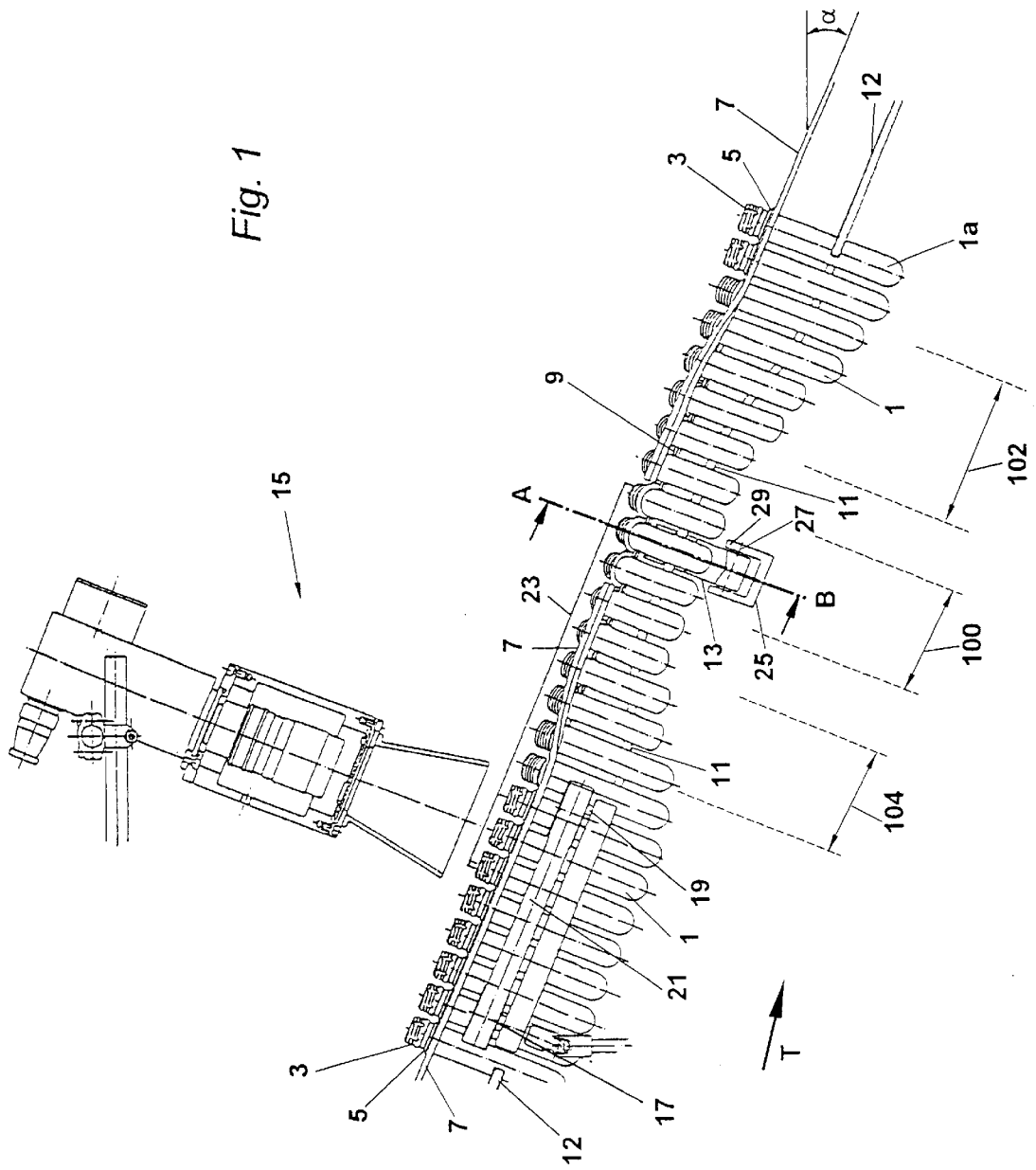
FIG. 1 depicts a side view of a portion of a device according to the invention.

FIG. 1 depicts a section of a conveyor track of a device according to the invention which is inclined in the direction of transport. This conveyor track is located, for example, between a repository for plastic preforms 1 and a heating station. A blow molding device may be located downstream from the heating station. As the design of the repository, the heating station, and the blow molding device may conform to the state of the art, they are not depicted in the figures. The segment of the conveyor track depicted in FIG. 1 includes the upper guide rails 7 and 9, which are inclined at an angle α relative to the horizontal plane so that the plastic preforms 1 will slide forward automatically. The guide rail 9, which is at the top and rear when seen from the viewing direction depicted in FIG. 1, is designed to be continuous, while the front guide rail 7 is interrupted in the screening area 100.

The execution depicted also includes lower guide rails 11 and 12. Once again, the guide rail 11, which is at the rear when seen from the viewing direction depicted in FIG. 1, is continuous, while the front guide rail 12 is interrupted.

Figure 2:
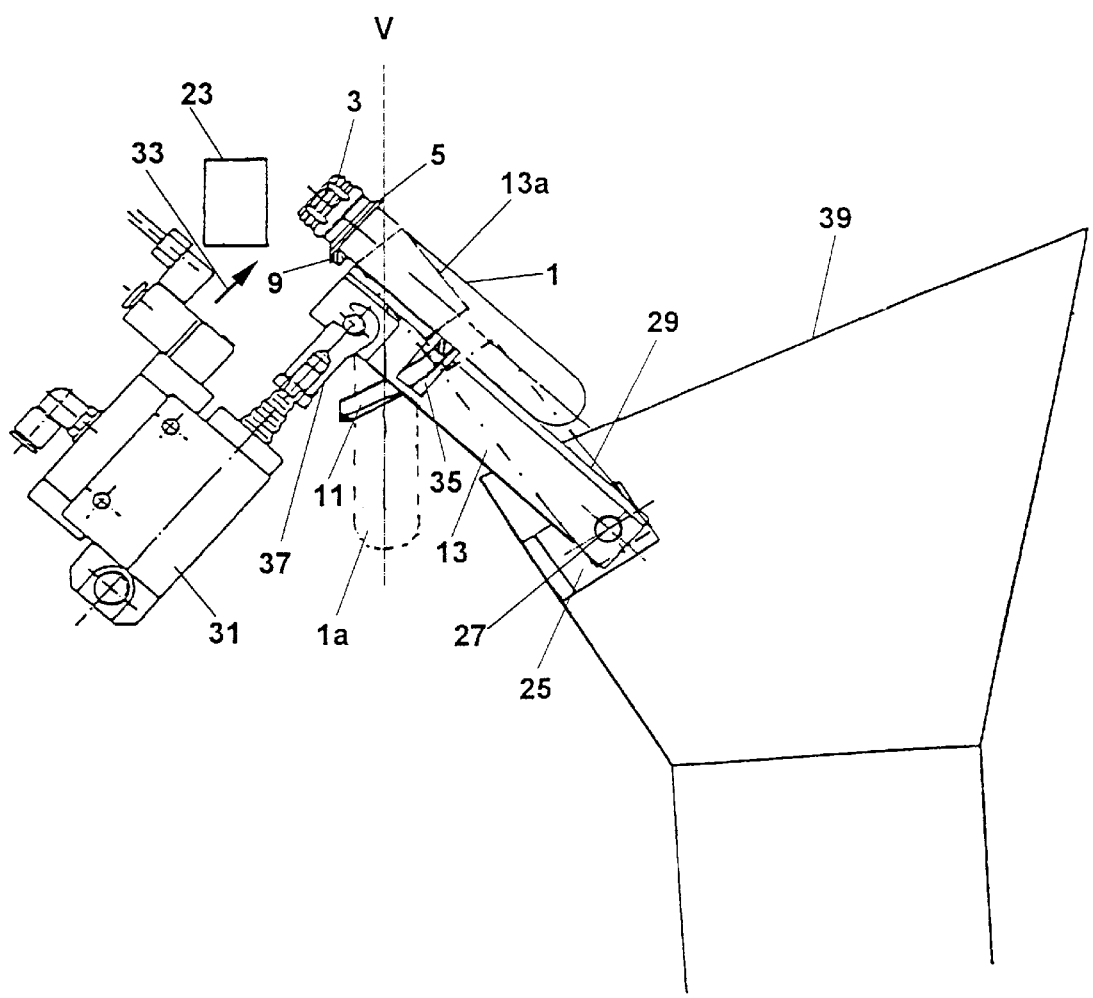
FIG. 2 depicts a cross-section in viewing direction A-B in FIG. 1.

The upper guide rails 9 and 7 are essentially parallel to one another, so that the plastic preforms 1, with their collars 5 positioned below the thread 3, move in a suspended fashion between the upper guide rails 7 and 9. In general, the lower guide rails 11 and 12 are arranged in such a way that they guide the plastic preforms in a position that falls essentially within the vertical plane V (FIG. 2). In the upswing area 104, the lower guide rail 11 is twisted out of the vertical plane V in such a way that it guides the plastic preforms 1 in a pivoted position in the direction T while the plastic preforms rest against the guide rail. Thus, in the screening area 100 the plastic preforms 1 assume a pivoted position with an angle of inclination of about 50 degrees relative to the vertical plane V. The convolution of the lower guide rail 11 is reversed in the downswing area 102, so that the plastic preforms 1 return to their primarily vertical position as they continue to move in the direction T.

In the execution depicted, the guide rails are essentially rectangular in profile. As is evident in FIGS. 1 and 2, these rectangular profiles follow the slope of the plastic preforms 1 along their track in the upswing area 104, the screening area 100, and the downswing area 102.

The reference number 15 refers to a CCD camera positioned upstream from the screening area. This CCD camera 15 faces the mouth area of the plastic preforms 1 from above. The CCD camera 15 acts as the inspection station. Additional inspection devices, e.g., for the lateral surfaces of the preforms, may be provided. A driving mechanism consisting primarily of a continuous belt 21 that travels around a deflection roller 19 and a driving roller 17 is located in the area of the inspection station 15 along the lateral surfaces of the plastic preforms 1. This driving mechanism is used to set a precisely defined speed, which is advantageous in the area of the inspection station 15.

A multiple photoelectric barrier 23 is used to monitor the path of the plastic preforms 1 from the inspection station 15 to the screening area 100. In the interest of simplification, the multiple photoelectric barrier 23 is only depicted in schematic form in the figures. It may, for example, consist of pairs of light sources and receivers that react to plastic preforms 1 being moved past them.

The screening apparatus is located in the screening area 100. In the execution depicted, this apparatus consists of a pusher 13 which pivots around an axis 27 held in a bearing block 25. The pusher 13 features a prismatic surface that faces the conveyor track for the plastic preforms 1.

In the cross-section along line A-B in FIG. 1 depicted in FIG. 2, this pusher 13 is visible in the viewing direction of transport. The pusher 13 is connected to a tappet 37 driven by a pneumatic cylinder 31. The reference number 33 applies to the direction of motion of the tappet 37 when it is used for screening purposes. The dotted line with reference number 13a indicates the position of the pusher 13 while it is screening out a plastic preform 1.

The pusher 13 features a slit 35 that encloses the lower guide rail 11. The dimensions of this slit 35 are such that the lower guide rail 11 does not obstruct the screening motion.

In the interest of simplification, only two plastic preforms 1, 1a are shown in the view depicted in FIG. 2. These plastic preforms are representative of the various positions of the plastic preforms along the belt. While plastic preform 1 in FIG. 2 is in a position in which it could be screened out, plastic preform 1a, which is indicated by dotted lines, has not been screened out and has already continued to travel along the downswing area 102 of the lower guide rail 11.

A screening container 39 into which the screened-out plastic preforms 1 fall is also depicted in FIG. 2.

This device operates as follows:

The plastic preforms 1 are automatically removed from a repository and suspended from the upper guide rails 7 and 9 in known fashion. Their collars 5 rest on both guide rails, which are still parallel to one another at this point. As a result of the slope of the conveyor track, they slide in this suspended position toward the inspection station which, in the example shown, consists of the CCD camera 15. In the area of the camera, the plastic preforms are gripped by the belt 21, which is driven by the driving roller 17. The belt 21 moves the plastic preforms 1 past the CCD camera 15 at a precisely defined speed.

In the execution described, the CCD camera 15, the multiple photoelectric barrier 23, and the pneumatic cylinder 31 are connected via signal lines to a shared control device not depicted in the figures. With the aid of a microprocessor, for example, this control device triggers the screening process as soon as a plastic preform detected by the CCD camera 15 as being defective has passed the multiple photoelectric barrier 23.

The CCD camera detects damage, irregularities, or defects, especially in the mouth area of the plastic preforms 1. A signal is triggered automatically as soon as a defect of this nature is detected. With the aid of the multiple photoelectric barrier 23, a control device can monitor the path of a plastic preform 1 identified as being defective by generating a counting pulse when this plastic preform 1 passes a photoelectric barrier. In this manner, the system can determine when the plastic preform 1 identified as being defective enters the screening area 100.

Downstream from the inspection station 15, the plastic preforms 1 are deflected from their vertical position by the lower guide rail 11. This is supported by the twisted shape of the support surfaces of the guide rails 7, 9, 11. The preforms 1 enter a pivoted position and roll uniformly downward in the direction of transport T along the guide rails 9 and 11, which are at the rear when seen from the viewing direction depicted in FIG. 1.

If a plastic preform 1, held in place only by the rear guide rails 9 and 11 in conjunction with the force of gravity and identified as being defective by the CCD camera 15, passes the multiple photoelectric barrier 23 and reaches a point in front of the prismatic surface 29 of the pusher 13, a pulse is transmitted to the pneumatic cylinder 31 so that the tappet 37 moves in direction 33. At the same time, the pusher 13 moves into position 13a (FIG. 2). As a result, the prismatic surface 29 hits the plastic preform 1 being screened out, causing the latter to lose its contact with the upper guide rail 9 on which the collar 5 is resting. The plastic preform 1 falls through the break in the upper guide rails 7, 12 and/or is forced through this break and drops into the screening container 39. After having been tapped, the pusher 13 returns to its home position so as not to affect the forward motion of the subsequent plastic preforms 1 in direction T. As a result of the slope of the conveyor track by an angle α relative to the horizontal plane, the subsequent plastic preforms 1 automatically slide forward, thus preventing a gap from occurring in the row.

Once they have passed the break in the upper guide rail 7, the plastic preforms 1 that have not been screened out reach the downswing area 102 in which the lower guide rail 11 is designed in such a way that it moves the plastic preforms 1 from their pivoted position back into the position located in the vertical plane V. This action is reinforced by the convolution of the upper support surfaces of the guide rails 7 and 9 apparent in FIGS. 1 and 2. Then the plastic preforms 1 are again guided by the upper guide rails 7 and 9, as well as by the lower guide rails 11 and 12.

As is apparent in FIG. 1, once they have passed the screening station described above the plastic preforms 1 that have not been screened out continue to move along a track tilted in the direction of transport T and then reach the heating station, where they are heated so that they can be inflated into their future shape in a subsequent blow molding station.

The execution described comprises an upper guide rail 9 and a lower guide rail 11 on which the plastic preforms 1 rest in the upswing area 104, in the screening area 100, and in the downswing area 102. In a modification of this execution, a convex surface may be provided that creates the sloped position of the plastic preforms 1 in the screening area. The plastic preforms roll down this surface in a manner similar to that in which they roll along the two guide rails 9 and 11. In this type of execution, the pusher 13 is provided in a gap in this surface, or it engages the threaded section protruding above the surface while the collar 5 rests on the upper edge of the surface.

What is claimed is:

1. Device for the manufacture of hollow plastic objects comprising in combination a conveyor track along which plastic preforms are transported in sequence past at least one inspection station to a molding station for molding the preforms into a desired shape, said conveyor track having a screening area (100) in which the preforms (1) are conveyed in such a way that they are loosely supported on only one side, and a screening apparatus (12, 31, 37) provided for said conveyor track that moves plastic preforms (1) that have been identified as being defective out of the row in response to signals from said inspection station (15).

2. Device according to claim 1, and a lever-like guide (9, 11) that guides the plastic preforms (1) in said screening area (100) into a pivoted position.

3. Device according to claim 2, wherein said lever-like guide (9, 11) in design in such a way that the tilt of the plastic preforms (1) in said screening area (100) amounts to approximately 50 degrees relative to a vertical plane (V) positioned in the direction of transport (T).

4. Device according to claim 2, wherein said device is used to process plastic preforms (1) with a collar (5), and wherein said lever-like guide (9, 11) comprises a guide edge for engaging the lower side of said collar (5) of the plastic preforms (1).

5. Device according to claim 4, wherein said lever-like guide comprises a surface against which the plastic preforms rest in a pivotal position in said screening area.

6. Device according to claim 4, wherein said lever-like guide comprises a first lower guide rail (11) which is arranged in such a way that a lower portion of the plastic preforms (1), which is spaced at a distance from said collar (5), rests against said first lower guide rail in said screening area (100) of said conveyor track in a pivoted position, and that said guide edge consists of a first upper guide rail (9).

7. Device according to claim 6, and a second upper guide rail (7) that engages the lower portion of said collar (5) of the plastic preforms (1), said second upper guide rail being positioned opposite said guide edge, wherein said second upper guide rail (7) is interrupted, at least in said screening area (100).

8. Device according to claim 7, and a second lower guide rail (12) that is located on the side of said conveyor track for the plastic preforms opposite said first lower guide rail (11) and is interrupted.

9. Device according to claim 4, wherein said lever-like guide (9, 11) is shaped in such a way that it moves the plastic preforms (1) from a suspended position located essentially in a vertical plane (V) into the pivoted position in said screening area (100), while the plastic preforms move along said lever-like guide (9, 11).

10. Device according to claim 9, wherein said lever-like guide (9, 11) is also shaped in such a way that after leaving said screening area (100) the plastic preforms (1, 1a) return to the suspended position located essentially in the vertical plane (V).

11. Device according to claim 9 or 10, wherein one of said guide rails (7, 9, 11) has support surfaces against which the plastic preforms (1) rest, wherein said support surfaces are twisted along said conveyor track in such a way that said support surfaces follow the pivoting motion of the plastic preforms (1).

12. Device according to claim 4, wherein said screening apparatuses comprise a pusher (13) operable to give a plastic preform (1) a lateral push in response to an error signal from at least one said inspection station (15) and thereby disengage said collar (5) from said guide edge (9).

13. Device according to claim 12, and a pneumatic cylinder (31) which is controlled by signals from said inspection station (15) for purposes of driving said pusher (13).

14. Device according to claim 12 or 13, wherein said pusher (13) comprises a prismatic surface (29) that engages the plastic preform (1) during the push.

15. Device according to claim 12 or 13, wherein said pusher (13) comprises a lever that pivots around a swiveling axis (27).

16. Device according to claim 1, wherein said inspection station (15) is arranged upstream from said screening area (100).

17. Device according to claim 16, and an apparatus for monitoring the path of a plastic preform (1) identified as being defective by said inspection station (15) as the preform travels from said inspection station (15) to said screening area (100).

18. Device according to claim 17, wherein said monitoring apparatus comprises a multiple photoelectric barrier (23).

19. Device according to claim 1, wherein said conveyor track is inclined in the direction of transport.

20. Device according to claim 1, wherein said inspection station comprises a CCD camera (15).

21. Device according to claim 1, and a driving apparatus (17, 19, 21) in the area of said inspection station (15) that generates a defined speed of the plastic preforms (1).

22. Device according to claim 21, wherein said driving apparatus comprises a driven belt (21) that engages the lateral surfaces of the plastic preforms (1).

23. Device according to claim 1, and a collection apparatus (39) for collecting plastic preforms (1) that have been screened out.

24. Process for the manufacture of hollow plastic objects comprising the steps of: transporting plastic preforms in a row along a conveyor track past at least one inspection station to a molding station for molding the preforms into a desired shape, conveying the plastic preforms (1) in a screening area (100) in such a way that they are loosely supported on only one side, and removing from the row those plastic preforms to be screened out in response to an error signal from the inspection station (15).

25. Device according to claim 1, wherein said hollow plastic objects are stretch-blown plastic bottles.

26. Device according to claim 1, where there are at least two said inspection stations.

27. Device according to claim 8, wherein said second lower guide rail is interrupted in said screening area (100).

* * * * *

UNITED STATES PATENT AND TRADEMARK OFFICE
CERTIFICATE OF CORRECTION

PATENT NO.   : 6,189,701 B1                                        Page 1 of 1
DATED        : February 20, 2001
INVENTOR(S)  : Horst Winter It is certified that error appears in the above-identified patent and that said Letters Patent is hereby corrected as shown below:

Column 5,
Line 60, "lower" should be -- upper --.

Claim 3,
Line 2, "in design" should be -- is designed --.

Claim 5,
Line 3, "pivotal" should be -- pivoted --.

Claim 8,
Line 3, after "preforms", add -- (1) --.

Signed and Sealed this

Eighth Day of January, 2002

Attest:

JAMES E. ROGAN
Attesting Officer    Director of the United States Patent and Trademark Office